United States Patent [19]

Harvey et al.

[11] 4,455,294
[45] Jun. 19, 1984

[54] STABLE DENTIFRICE CONTAINING ACIDIC SILICEOUS POLISHING AGENT

[75] Inventors: Kenneth Harvey, Wilmslow; Stephen T. Connors, Sale, both of England

[73] Assignee: Colgate-Palmolive Company, New York, N.Y.

[21] Appl. No.: 442,475

[22] Filed: Nov. 17, 1982

[51] Int. Cl.³ .......................... A61K 7/16; A61K 7/18
[52] U.S. Cl. .................................. 424/52; 206/524.1; 206/524.4; 424/49; 424/57
[58] Field of Search ................................... 424/47–55; 206/524.1, 524.4

[56] References Cited

U.S. PATENT DOCUMENTS

| | | | |
|---|---|---|---|
| 3,678,155 | 7/1972 | Clippingdale et al. | 424/52 |
| 3,864,470 | 2/1975 | Watson | 424/49 |
| 3,906,090 | 9/1975 | Colodney | 424/52 |
| 3,911,102 | 10/1975 | Harrison | 424/49 |
| 3,939,262 | 2/1976 | Kim | 424/52 |
| 4,123,517 | 10/1978 | Baines et al. | 424/57 |
| 4,141,969 | 2/1979 | Mitchell | 424/52 |
| 4,159,280 | 6/1979 | Wason | 206/524.4 |
| 4,238,476 | 12/1980 | Harvey | 424/52 |
| 4,263,276 | 4/1981 | Harvey | 424/52 |
| 4,305,928 | 12/1981 | Harvey | 424/52 |
| 4,314,990 | 2/1982 | Denny et al. | 424/52 |
| 4,328,205 | 5/1982 | Taylor | 424/52 |
| 4,340,583 | 7/1982 | Wason | 424/52 |
| 4,340,584 | 7/1982 | Wason | 424/52 |
| 4,356,168 | 10/1982 | Harvey et al. | 424/52 |

*Primary Examiner*—Shep K. Rose
*Attorney, Agent, or Firm*—Robert L. Stone; Murray M. Grill; Herbert S. Sylvester

[57] ABSTRACT

There is disclosed a dentifrice formulation which is stable in the sense of not producing gassing as evidenced by visually discernable distention over a period of 168 days at 43° C. in an unlined aluminum tube.

The formulation comprises an aqueous dentally acceptable oral vehicle at least 27.5% by weight of the dentifrice comprising water and dispersed in the said oral vehicle from 10 to 40% by weight of the dentifrice of a neutral siliceous polishing agent having a stirred slurry pH (as herein defined) in the range from 5 to less than 6.5, and a stabilizing amount of monofluorophosphate ion, the dentifrice having a stirred slurry pH in the range from 5.5 to 8.

12 Claims, No Drawings

STABLE DENTIFRICE CONTAINING ACIDIC SILICEOUS POLISHING AGENT

This invention relates to a stable dentifrice and in particular to a dentifrice which can be used in an unlined aluminium tube.

According to the present invention a stable dentifrice comprises an aqueous dentally acceptable oral vehicle, at least 27.5% and typically 30 to 60%, preferably 40 to 55% for example about 45% by weight of the dentifrice comprising water and dispersed in the said oral vehicle from 10 to 40%, preferably 10 to 30% and especially 15 to 25% by weight of the dentifrice of an acidic siliceous e.g. alkali metal aluminosilicate, polishing agent characterised as having a stirred slurry pH (as defined herein) in the range from 5 to less than 6.5 preferably 5 to 6.4 e.g. 5.1, 5.2, 5.3 or 5.4 to 6.3, 6.2, 6.1 or 6.0 especially 5.5 to 6.0 particularly 5.7 to 5.9, and a stabilizing amount of mono-fluorophosphate ion, the dentifrice having a stirred slurry pH in the range 5.5 to 8, preferably 6.5 to 7.5, and especially 6.7 to 7.3, optionally a non-toxic amount of at least 0.2% by weight of the dentifrice of chloroform, and desirably, at least when chloroform is present, from 0.05 to 5% by weight of the dentifrice of a stabilizing anionic phosphate ester mixture, the said mixture comprising monoester of the formula:

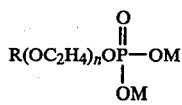

and diester of the formula:

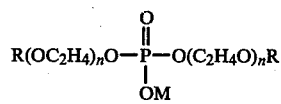

wherein R is an alkyl group of 10 to 20 carbon atoms; n is a number from 1 to 6; and M is hydrogen, alkali metal or ammonium. The stabilizing anionic phosphate ester mixture reduces or prevents corrosion in the presence of chloroform and stabilises the dentifrice.

It is an advantage of this invention that a stable dentifrice containing siliceous polishing agent is provided.

The stability with which the present invention is concerned is the substantial absence of gas generating reactions between the components of the dentifrice and the aluminium surface of an unlined aluminium tube as shown by the absence of visually discernable distension of the closed toothpaste tube containing the dentifrice when the said tube has been held at 43° C. for 168 days.

The invention also extends to an unlined aluminium tube filled with a stable dentifrice in accordance with the present invention.

The stabilizing mono-fluorophosphate ion may be provided by any appropriate compound thereof but a particularly convenient compound is sodium mono-fluorophosphate.

This may be used in any amount having the necessary defined stabilizing effect on the particular embodiment of the dentifrice according to the invention but amounts providing at least 0.01% mono-fluorophosphate ion are prudently used and for greater certainty at least 0.05% or at least 0.075, or 0.09%, should be used. Sodium monofluorophosphate will provide such amounts of the monofluorophosphate ion when present in amounts of 0.076, 0.38, 0.57, or 0.68% respectively. Use of 0.7 to 0.8% of sodium monofluorophosphate has been found particularly effective and thus a preferred proportion thereof is at least 0.7%. Higher amounts are not precluded but an upper limit of 7.6% will usually not be exceeded.

The polishing material employed in the present invention is an acidic siliceous material which may contain a small amount e.g. up to about 10% or somewhat more of alumina interbonded in the silica lattice. It can be further characterised as being synthetic and amorphous and as having a refractive index between about 1.4 and 1.5.

If desired, other polishing agents which as individual components do not contribute substantially to instability or corrosivity with an unlined aluminium surface may also be present. Such additional polishing agents include dicalcium phosphate dihydrate and anhydrous dicalcium phosphate as well as tricalcium phosphate, calcium pyrophosphate and calcined alumina. When an additional polishing agent is present, the amount of polishing material in the dentifrice may amount to up to about 75% by weight preferably 30 to 55% of the dentifrice.

When chloroform is present in the formulation it is employed in a non-toxic amount which is effective to provide flavour to the dentifrice. However since chloroform in combination with the siliceous polishing agent results in instability and corrosion in the presence of an unlined aluminium surface an appropriate stabilizing amount of an anionic phosphate ester mixture is also incorporated in such chloroform containing formulations. The chloroform may be present in an amount as low as about 0.2% by weight of the dentifrice and as high as 8% by weight or more. An amount of chloroform in the range of 0.5 to 3.5% by weight is preferred. It is noted that in view of the toxic properties of large amounts of chloroform some countries have or are establishing legal limits on the maximum amount of chloroform which can be used in products such as dentifrices, providing a safety margin by not approaching the toxic threshold too closely. However, even given such legal maxima, the effect of the stabilizing phosphate ester can be observed when non-toxic amounts such as 8%, 5%, 3.5%, 0.5% or 0.2% by weight of chloroform are present.

The anionic phosphate esters are mixtures of mono and di-esters of the formulas set forth above. Suitable esters are available from MoDo Kemi Aktiebolaget, formerly Berol Aktiebolaget, of Sweden under the name BEROL (BEROL is a trade mark) and may include an anionic triester moiety too, as well as some non-ionic portion. BEROL 729 has alkyl chain lengths of 16 to 18 carbon atoms and contains series of 4 ethylene oxide units. BEROL 729 is generally used in neutralised or partially neutralised form.

Further anionic phosphate esters which may be used in acid or neutralised forms are BEROL 525 which contains alkyl groups of 10 to 18 carbon atoms and series of 5 ethylene oxide units and BEROL 513 which also contains alkyl groups of 16 to 18 carbon atoms. However, BEROL 525, is also preferred in neutralised or partially neutralised form. Further BEROL anionic phosphate esters are available as BEROL 521, BEROL 724 and BEROL 733. The weight ratio of monoester to diester may vary, typically from about 1:10 to 10:1.

When the acid forms of the anionic phosphate ester surface active agents are neutralised or partially neutralised, alkali metal, preferably sodium, or ammonium cations are present.

Desirably the stirred slurry pH of the completed dentifrice is in the range from 6.5 to 8, preferably 6.5 to 7.5.

The preferred anionic phosphate ester is BEROL 513.

The anionic phosphate ester, when present, is used in an amount up to about 5% by weight effective to stabilize the dentifrice in an unlined aluminium tube. This amount can be as little as about 0.05% and would depend, at least in part on the amounts of chloroform and siliceous polishing agent present. For instance with about 3.5% chloroform, it would be desirable to employ about 1.5% of the anionic phosphate ester. A typical ester content would be in the range of 0.1 to 2% by weight, preferably 0.5 to 1.5%, of the dentifrice.

Besides stabilizing the dentifrice the anionic phosphate ester also provides surface active properties. Such surface active properties are described in British Patent Specifications Nos. 1475251 and 1475252.

The dentifrice as mentioned above contains a high proportion of a liquid vehicle which may comprise water, in amount of at least 27.5% by weight of the preparation. The liquid vehicle may additionally or alternatively comprise humectants such as glycerine, but unlike conventional high liquid vehicle dentifrices can dispense with such humectants as sorbitol solution or propylene glycol. A mixture of water and glycerine is particularly advantageous.

The solid portion of the vehicle of the dentifrice is a gelling agent or binder such as hydroxyethyl cellulose or hydroxypropyl cellulose, Irish moss, gum tragacanth, sodium carboxymethyl cellulose, polyvinyl pyrrolidone, xanthan, starch or water-soluble hydrophilic colloidal carboxyvinyl polymers such as those sold as CARBOPOL 934 and 940 (CARBOPOL is a trade mark).

The dentifrices will include an organic surface active agent which can be replaced by the anionic phosphate ester stabilizing agent if such is present, or retained. Such additional agent may be anionic, nonionic, cationic or ampholytic in nature, and it is preferred to employ as the surface active agent a detersive material which imparts to the dentifrice detersive and foaming properties. Suitable types of such detergents are water-soluble salts of higher (i.e. having at least 12 carbon atoms) fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as a sodium olefin sulphonate in which the olefin group contains 12-21 carbon atoms, higher alkyl sulphoacetates, higher fatty acid esters of 1,2-dihydroxy propane sulphonates, and the substantially saturated higher aliphatic acyl amides of lower (i.e. having not more than 4 carbon atoms) aliphatic amino carboxylic acid compounds, such as those having 12 to 16 carbons in the fatty acid, alkyl or acyl radicals. Examples of the last mentioned amides are N-lauroyl sarcosine, and the sodium, potassium and ethanolamine salts of N-lauroyl, N-myristoyl or N-palmitoyl sarcosine, which should be substantially free from soap or similar higher fatty acid material which tends to substantially reduce the effect of these compounds. The use of these sarcosine compounds in dentifrices is particularly advantageous since these materials exhibit a prolonged and marked effect in the inhibition of acid formation in the oral cavity due to the carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene glycol ("Pluronics"—PLURONIC is a Trade Mark) and amphoteric agents such as quaternised imidazole derivatives, which are available under the trade mark MIRANOL such as MIRANOL C2M. Cationic surface active germicides and anti-bacterial compounds such as diisobutylphenoxyethoxyethyl dimethyl benzyl ammonium chloride, tertiary amines having one fatty alkyl group (of from 12-18 carbon atoms) and two (poly)oxyethylene groups attached to the nitrogen (typically containing a total of from 20 to 50 ethanoxy groups per molecule) and salts thereof with acids, and compounds of the structure

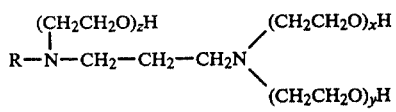

wherein R is a fatty alkyl group typically containing from 12 to 18 carbon atoms, and x, y and z total 3 or higher, as well as salts thereof with mineral or organic acids, may also be used.

The total amount of surface active agent, including the anionic phosphate ester, if present, typically does not exceed about 5%.

In certain forms of this invention, in addition to the source of mono-fluorophosphate ion, a fluoride-providing compound is present in the oral preparation. These compounds may be slightly soluble in water or may be fully water-soluble. They are characterised by their ability to release fluoride ions in water and by substantial freedom from reaction with other compounds of the oral preparation. Among these materials are organic amine fluorides such as cetylamine hydrofluoride and bis (hydroxyethyl)-aminopropyl-N-hydroxy-ethyl-octadecyl-amine dihydrofluoride or inorganic fluoride salts, such as suitable alkali metal, alkaline earth metal, and heavy metal salts, for example, sodium fluoride, potassium fluoride, ammonium fluoride, a copper fluoride, such as cuprous fluoride, zinc fluoride, a tin fluoride such as stannous fluoride, or stannous chlorofluoride, sodium fluorosilicate, ammonium fluorosilicate, sodium fluorozirconate, aluminium mono and di-fluorophosphate, and fluorinated sodium calcium pyrophosphate. Alkali metal and tin fluorides are preferred. A mixture of sodium fluoride and sodium monofluorphosphate is also highly desirable.

The amount of the fluorine-providing compound is dependent to some extent upon the type of compound, its solubility, and the type of oral preparation, but it must be a non-toxic amount. It is considered that an amount of such compound which releases a maximum of 1% by weight of fluoride ion, based on the weight of the preparation, is satisfactory. Any suitable minimum amount of such compound may be used, but it is preferable to employ sufficient compound to release from 0.005% to 1%, most preferably about 0.1%, by weight of fluoride ion. Typically, in the cases of alkali metal fluoride and stannous fluoride, this component is present in an amount up to 2% by weight, based on the weight of the preparation, and preferably in the range of from 0.05% to 1%.

Antibacterial agents may also be present, typically in an amount of 0.01–5% by weight. Typical antibacterial agents include $N^1$-(4-chlorobenzyl)-$N^5$-(2,4-dichlorobenzyl) biguanide;
p-chlorophenylbiguanide;
4-chlorobenzhydrylbiguanide;
4-chlorobenzhydrylguanylurea;
N-3-lauroxypropyl-$N^5$-p-chlorobenzylbiguanide;
1,6-di-p-chlorophenylbiguanidohexane; (chlorhexidine);
1,6-bis(2-ethylhexylbiguanido)hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine;
and their non-toxic acid addition salts.

Various other materials may be incorporated in the oral preparations of this invention as adjuvants. Examples are colouring or whitening agents, preservatives, silicones, chlorophyll compounds, and ammoniated material such as urea, diammonium phosphate, and mixtures thereof.

These adjuvants, where present, are incorporated in the preparations in amounts which do not substantially adversely affect the properties and characteristics desired. Whitening agents such as titanium dioxide or zinc oxide, typically in amount of 0.2 to 1% by weight provide a particularly fine cosmetic appearance to the dentifrice.

The dentifrice will usually contain flavouring and/or sweetening material, in addition to any chloroform which may be employed. Examples of suitable flavouring constitutents are flavouring oils, e.g. oils of spearmint, peppermint, wintergreen, sassafras, clove, sage, eucalyptus, marjoram, cinnamon, lemon and orange, and methylsalicylate. Suitable sweetening agents include sucrose, lactose, maltoses, sorbitol, sodium cyclamate, perillartine and saccharin. Suitably flavour and sweetening agents may together comprise from 0.01% to 5% or more of the preparation.

The dentifrice is typically prepared by dispersing the polishing material (and when chloroform is to be present the phosphate ester) in the dental vehicle and other components, (except for the chloroform) and then subjecting the mixture of deaeration after which any chloroform which is to be incorporated may be introduced in a closed vacuum system.

The dentifrice is then placed in an aluminium tube.

Due to the compositions stability to aluminium, the inner surface of the aluminium tube need not be provided with a lining and thus the tubes can be unlined aluminium tubes.

However the stability of the composition is of benefit even when lined tubes are to be used because in this case gassing of such tubes in which the lining may be defective or damaged in use so as to expose the aluminium surface is avoided. Also the invention permits the use of its chloroform containing embodiments in tubes which, although lined, use linings which can be penetrated by chloroform or its breakdown products.

The invention may be put into practice in various ways and one specific embodiment will be described to illustrate the invention with reference to the accompanying Example All amounts and proportions given in this specification are by weight unless otherwise indicated.

EXAMPLE

The dentifrice formulation given in Table 1 below was prepared in conventional manner by mixing the ingredients together and allowing them to gel with the water for 15 minutes at 45° to 50° C. after which the gelled blend was mixed to adequately disperse the powders.

The Table gives the composition and initial properties of the dentifrice formulation.

The pH measurement of solids as slurries may be liable to variation depending on how the slurry is made up and we thus prefer to define the technique used for pH measurement herein.

The pH values both for the sodium alumino silicate (SAS) and the dentifrice formulation were measured on KENT Model No. 7060 pH meter using an ORION combination electrode calibrated at pH 9.2±0.1 at 20° C. using British Drug Houses borate buffer and at pH 7.0±0.1 at 20° C. using BDH phosphate buffer.

A 20% aqueous slurry in distilled water of the test material was then made up and stirred for 10 minutes using a magnetic stirrer prior to determination of the pH at 20° C. A pH measured this way will be referred to herein as a stirred slurry pH.

The following points should be noted about the data in Table 1.

Note 1:
The sodium carboxymethyl cellulose is grade 7 MF.

Note 2:
The % soluble fluoride value given is the (average of two readings) $\times 10^2$, i.e. a figure of 10 in Table 1 means an average fluoride content of 0.10.

Note 3:
The pH for the dentifrice was measured immediately after the dentifrice had been made up.

The dentifrice formulations given in the Table is filled in conventional manner into unlined aluminum tubes.

TABLE 1

| COMPONENT | AMOUNT |
|---|---|
| Glycerine | 25.00 |
| Sodium Carboxymethyl Cellulose - (1) | 1.00 |
| Titanium Dioxide | 0.40 |
| Sodium Saccharin | 0.18 |
| Sodium Mono-fluorophosphate | 0.76 |
| % soluble fluoride (2) | 10.7 |
| Water | 42.16 |
| Sodium Aluminosilicate (SAS) | 24.00 |
| SAS Type | Dentolex 644 |
| pH of SAS | 5.8 |
| Sodium Lauryl Sulphate | 1.50 |
| Water | 4.00 |
| Flavour | 1.00 |
| pH of dentifrice - (3) | 6.6 |

The dentifrice formulation of the Example aged well in the unlined aluminium tubes over a three month period at 43° C., and though it contained some hard lumps throughout this period and suffered some yellowing at the end, there was no gassing.

This lumpiness is thought to be due to some oversize particles being present in the Dentolex 644 SAS material used and it may be that this problem could be overcome by sieving of this SAS material.

Dentolex 644 may be obtained from Zeofinn Oy, of Hainina, Finland and the manufacturers describe it as having the following characteristics:

| Chemical Composition | Sodium Silico Aluminate |
|---|---|
| Primary Particle Diameter | 0.016 microns |
| Moisture Loss | Not more than 7% on heating to 105° C. for 2 hours. |
| Density | 2.0 g/cm$^3$ at 25° C. |
| Bulk Density | 300 Kg/m$^3$ as packed |
| Oil Absorption | 170 ml oil/100 g |
| Refractive Index | 1.47 at 20° C. |

We claim:

1. A stable dentifrice contained in an unlined aluminium tube consisting essentially of an aqueous dentally acceptable oral vehicle, at least 27.5% by weight of the dentifrice comprising water and dispersed in the said oral vehicle from 10 to 40% by weight of the dentifrice of an acidic sodium aluminosilicate polishing agent containing about 4% total aluminium as Al and having a stirred slurry pH (as herein defined) in the range from 5 to less than 6.5, and a stabilizing amount of monofluorophosphate ion, the dentifrice having a stirred slurry pH in the range from 5.5 to 8, said monofluorophosphate ion stabilizing said dentifrice against gas generating reaction between the components of said dentifrice when said dentifrice is in contact with the surface of said unlined aluminium tube.

2. A dentifrice as claimed in claim 1 in which the dentifrice comprises at least 30% by weight of water.

3. A dentifrice as claimed in claim 2 in which the dentifrice comprises 35 to 60% by weight of water.

4. A dentifrice as claimed in claim 3 in which the dentifrice comprises 40 to 55% by weight of water.

5. A dentifrice as claimed in claim 1 in which the polishing agent comprises 10 to 30% by weight of the dentifrice.

6. A dentifrice as claimed in claim 5 in which the polishing agent comprises 15 to 25% by weight of the dentifrice.

7. A dentifrice as claimed in claim 1 in which the stirred slurry pH of the polishing agent is in the range 5.0 to 6.4.

8. A dentifrice as claimed in claim 7 in which the stirred slurry pH of the polishing agent is in the range 5.5 to 6.0.

9. A dentifrice as claimed in claim 1 comprising at least 0.01% of mono-fluorophosphate ion.

10. A dentifrice as claimed in claim 9 comprising at least 0.05% of mono-fluorophosphate ion.

11. A dentifrice as claimed in claim 10 comprising at least 0.09% of mono-fluorophosphate ion.

12. A dentifrice comprising 35% to 50% by weight water, 0% to 30% by weight, 15 to 25% of sodium aluminosilicate polishing agent containing about 4% total aluminium as Al and having a stirred slurry pH in the range 5.0 to 6.4, at least 0.5% by weight of alkali metal monofluorophosphate, calcined alumina in an amount in the range 0% to 15% by weight and one or more organic surface active agents in an amount not in excess of 5% by weight, the dentifrice having a stirred slurry pH in the range 5.5 to 8, said monofluorophosphate ion stabilizing said dentifrice against gas generating reaction between the components of said dentifrice when said dentifrice is in contact with the surface of said unlined aluminium tube.

* * * * *

UNITED STATES PATENT AND TRADEMARK OFFICE
CERTIFICATE OF CORRECTION

PATENT NO. : 4,455,294

DATED : June 19, 1984

INVENTOR(S) : Harvey and Connors

It is certified that error appears in the above-identified patent and that said Letters Patent are hereby corrected as shown below:

Cover page, below "[22] Filed: Nov. 17, 1982", insert

-- [30]   Foreign Application Priority Data

Nov. 19, 1981 [GB]   United Kingdom................ 8134926--.

Signed and Sealed this

Twenty-seventh Day of November 1984

[SEAL]

Attest:

GERALD J. MOSSINGHOFF

Attesting Officer

Commissioner of Patents and Trademarks